US006884256B2

(12) United States Patent
Huang et al.

(10) Patent No.: US 6,884,256 B2
(45) Date of Patent: Apr. 26, 2005

(54) MULTIPLE-EFFECT HEALTH DEVICE

(76) Inventors: Chuan-Chi Huang, No. 6-2 (B1), Tan-Yany Street, Taipei (TW); Kuo-Yuan Chan, No. 209, Yen-Lu Road, Sec. 2, Pu-Hsin Hsiang, Chang-Hua Hsien (TW)

( * ) Notice: Subject to any disclaimer, the term of this patent is extended or adjusted under 35 U.S.C. 154(b) by 175 days.

(21) Appl. No.: 10/336,395

(22) Filed: Jan. 3, 2003

(65) Prior Publication Data

US 2004/0133252 A1 Jul. 8, 2004

(51) Int. Cl.[7] .................................................. A61F 7/12
(52) U.S. Cl. .......................... 607/96; 607/100; 600/26; 600/27; 600/28
(58) Field of Search ............................. 607/88, 90, 91, 607/96, 100; 600/26–28

(56) References Cited

U.S. PATENT DOCUMENTS

| 5,787,525 A | * | 8/1998 | Sugihara et al. ............... 5/421 |
| 6,516,229 B1 | * | 2/2003 | Wey ........................... 607/100 |
| 2004/0001707 A1 | * | 1/2004 | Ryu et al. ................... 392/385 |

* cited by examiner

Primary Examiner—Rosiland Rollins

(57) ABSTRACT

A health device includes: a far-infrared massaging device for a user's leaning, seating or lying thereon and for intimately radiating far-infrared rays towards the user to improve the user's blood circulation and metabolism for enhancing his or her health; and a juxtapositional far-infrared and anion generator movably juxtapositioned to the far-infrared massaging device for radiating far-infrared rays towards the user and for releasing anions into the air for deodorizing the air surrounding the user for synergetically promoting the user's health.

3 Claims, 4 Drawing Sheets

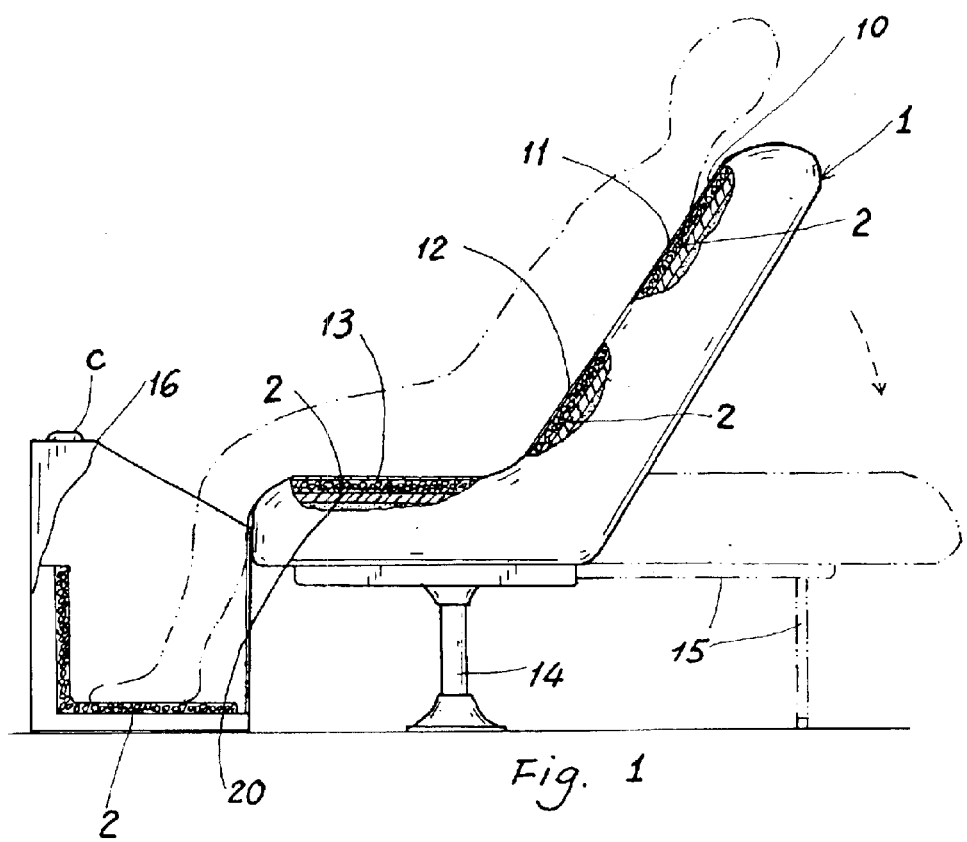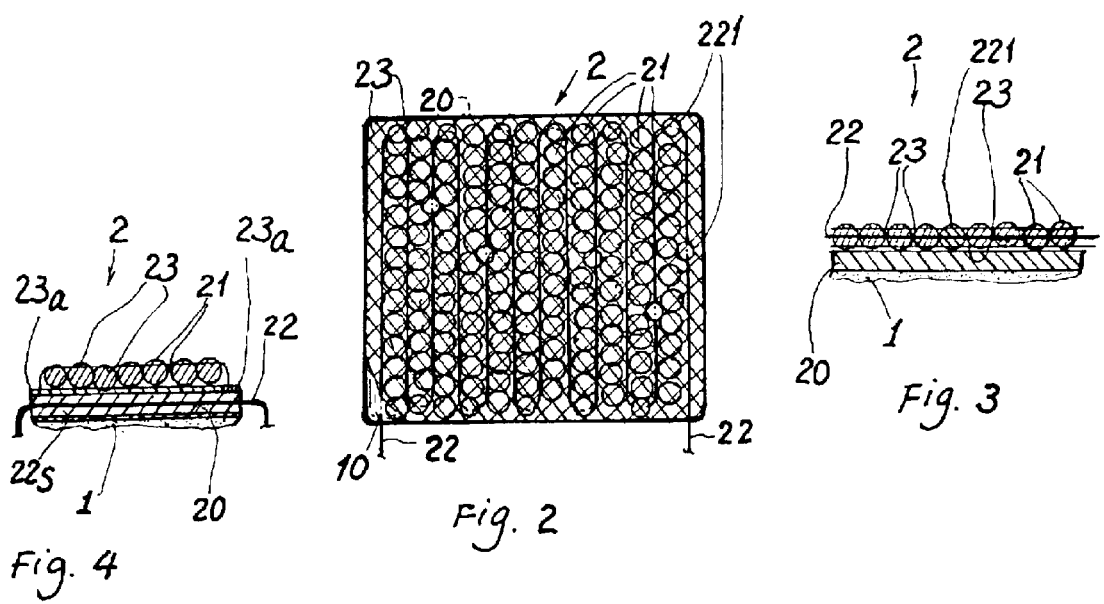

MULTIPLE-EFFECT HEALTH DEVICE

BACKGROUND OF THE INVENTION

The far-infrared rays have been known to help improve the circulation of a human blood and to improve his or her metabolism, thereby enhancing human health. However, a conventional health device for emitting far-infrared rays such as a conventional far-infrared sauna device may only provide far-infrared rays radiating to the user, it can not simultaneously provide a physical massage effect for the user, thereby limiting its health-enhancing effect.

A conventional air cleaner may release anions which are helpful for human health by reducing odor or inhibiting bacteria in the air. However, it may also release ozone or high-concentration peroxides into air to be hazardous to human health.

The present inventor has found the drawbacks of the conventional health devices and invented the present health device overcoming the drawbacks of the conventional health devices.

SUMMARY OF THE INVENTION

The object of the present invention is to provide a health device including: a far-infrared massaging device for a user's leaning, seating or lying thereon and for intimately radiating far-infrared rays towards the user to improve the user's blood circulation and metabolism for enhancing his or her health; and a juxtapositional far-infrared and anion generator movably juxtapositioned to the far-infrared massaging device for radiating far-infrared rays towards the user and for releasing anions into the air for deodorizing the air surrounding the user for synergetically promoting the user's health.

BRIEF DESCRIPTION OF THE DRAWINGS

FIG. 1 is a partial cut-away illustration of the far-infrared massaging means of the present invention.

FIG. 2 is a plan view of a far-infrared actuation unit as provided in the far-infrared massaging means as shown in FIG. 1.

FIG. 3 is a partial sectional drawing of the far-infrared actuation unit as shown in FIG. 2.

FIG. 4 is a partial sectional drawing of another preferred far-infrared actuation unit in accordance with the present invention.

DETAILED DESCRIPTION

Figure 5:
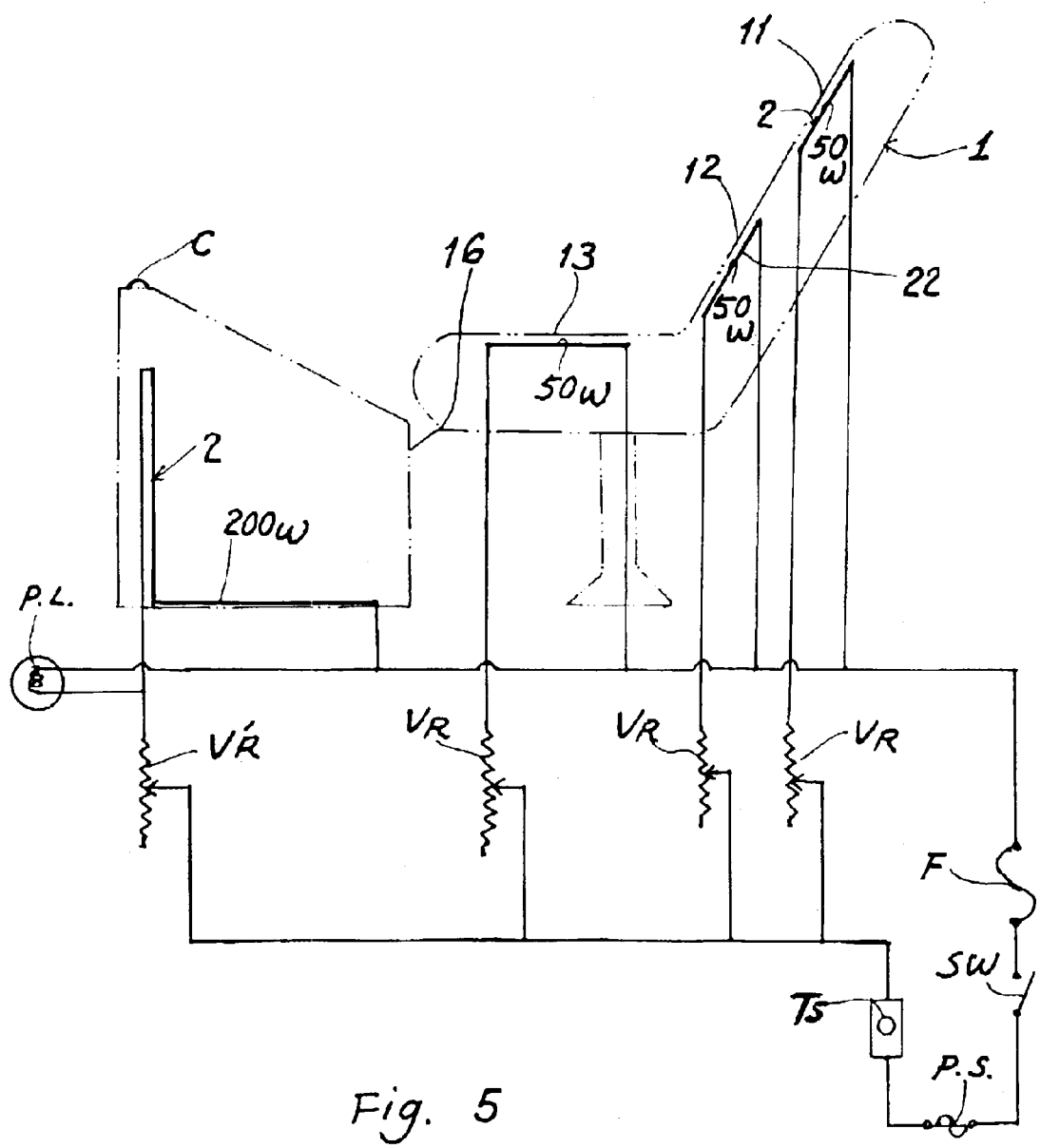
FIG. 5 is an electric circuit diagram of the massaging means as shown in FIG. 1.

As shown in the drawing figures, a multiple-effect health device of the present invention comprises: a far-infrared massaging means 1 having a plurality of far-infrared actuation units 2 formed or embedded in the massaging means 1 for a user's seating, leaning or lying on the massaging means 1 for warming and massaging the user for improving his or her health; and a juxtapositional far-infrared and anion generator 3 movably juxtapositioned to the massaging means 1 for radiating far-infrared rays towards the user and for releasing anions (minus ions) into the air for deodorizing the air to be inhaled by the user for enhancing his or her health.

The far-infrared massaging means 1 and the juxtapositional far-infrared and anion generator 3 may be together used or used separately, individually.

The far-infrared massaging means 1 as shown in FIGS. 1~5 comprises: a plurality of far-infrared actuation units 2 formed or embedded in the massaging means 1 formed as a foldable chair or bed including a back portion 11, a waist portion 12, a hip portion 13 and a foot warming box 16 attached to the chair or bed for contacting the user's back portion, waist portion and hip portion respectively on the back portion 11, the waist portion 12 and the hip portion 13 of the massaging means 1 and for accommodating the user's feet or legs into the warming box 16.

The far-infrared massaging means 1 includes: a supporting device 14 for supporting the massaging means, and an auxiliary supporting bracket 15 foldably formed on a bottom portion of the massaging means 1 for helping supporting of the massaging means 1 especially when horizontally positioned for the user's lying purpose.

Each far-infrared actuation unit 2, as shown in FIGS. 2, 3 as formed in the massaging means 1 and the warming box 16, includes: a plurality of far-infrared radiation beads or balls 21 (made of far-infrared radiation materials including Tourmaline) lain, formed, adhered or fixed on a base 20 which is embedded, inserted or formed in the massaging means 1 formed as a sofa chair or bed; at least an electric heating element (or wire) 22 formed in or through the plurality of far-infrared radiation beads or balls 21 and operatively powered for heating the far-infrared radiation beads 21 for emitting far-infrared rays (which have wave length ranging 8~14 microns) to radiate or penetrate into the user's body for warming, massaging the user for enhancing his or her health; and an infrared (IR)—penetrable cover or porous net 23 covering the far-infrared radiation beads 21 for preventing releasing of the beads 21 from the actuation unit 2.

The base 20 may be made of electrically insulative materials including foam, plastic and rubber materials and may be integrally formed with the cushioning material or filler provided in the massaging means 1.

The plurality of far-infrared radiation beads 21 are arranged to form a corrugated upper or outer surface for massaging or stimulating the user's body when seating, leaning or lying on the surface of the far-infrared radiation beads 21 as formed in the far-infrared actuation unit 2 which is provided in an upper portion of the massaging means 1, having an air and infrared penetrable sofa leather (or cover) 10 formed on a top of the massaging means 1 and partitioned between the user's body and the far-infrared actuation unit 2.

The cover or porous wire 10 is formed as a thin layer to soothe the pain caused by the corrugated surface of the far-infrared beads 21 of the actuation unit 2 when the user leans on the massaging means 1. Even the corrugated surface of the beads 21 is beneficial for the stimulating and massaging effect to the user's body, the acute protrusion of the corrugated surface may still stick the user's body to cause his or her pain, thereby requiring the thin-layer cover 10 to be partitioned between the user and the massaging beads 21.

The far-infrared radiation materials, namely the Tourmaline, will emit far-infrared rays especially when heated and will also release anions.

The Tourmaline can strongly emit the far-infrared rays to improve the user's blood circulation and metabolism to thereby enhance the user's health. Since the far-infrared rays as emitted from Tourmaline as used in the present invention are very strong, the rays may penetrate into user's body even wearing clothes. Therefore, the user may "enjoy" the warming and massaging effect of the present invention conveniently and comfortably without taking off his or her clothes.

The anions as released from Tourmaline may deodorize the air so that the user's feet when protruding into the interior of the warming box 16 having the far-infrared actuation unit 2 containing Tourmaline provided in the box 16 may maintain a good quality of the air in the box 16 since the air in the box 16 will be deodorized by the anions released by the Tourmaline. Besides, the Tourmaline will emit the far-infrared rays, as usual, to improve the blood circulation of the user's feet and legs to help enhance his or her health.

Accordingly, the present invention may enhance the user's health by improving his or her blood circulation and metabolism, by activating the cells, soothing the pain of muscle and nerve systems by the far-infrared rays as emitted from Tourmaline contained in the beads 21 and by the stimulation of the massaging effect as caused by the corrugated surface of the beads 21.

The electric heating element or wire 22 as shown in FIG. 2 is sinuously wound around (or in) the far-infrared beads 21 in the actuation unit 2 in a shape of sawtooth, corrugations, or square waves to thoroughly heat the beads 21 contiguous to the heating element or wire 22.

The heating element 22 may be inserted through the beads 21 or bead-like member to have a height of the heating element to be lower than a height of the bead 21 so that the heating element 22 may not directly contact the user's skin to prevent overheating or injury to the user.

The heating element 22 may be made of silicon-containing heating wire or any other heating materials for generating heat when electrically powered.

As shown in FIG. 4, the far-infrared radiation beads 21 may be secured or adhered on a heat-conducting pad 22s by net 23 or by thermally conductive adhesive 23a; and the heating element or wire 22 may then be formed on or in the heat-conducting pad 22s so that the heat produced from the heating element 22 will then be conducted and transferred to the beads 22 to heat the beads 21 in order to emit far-infrared rays strongly and effectively. Since the heating element or wire 22 is not directly contacted with the user's skin, the user will not be burned or injured by the heat of the heating element 22.

The heating elements 22 provided in the far-infrared actuation units 2 may be formed in the back portion 11, the waist portion 12, the hip portion 13 and the box 16 as parallelly connected to the electric circuit diagram as shown in FIG. 5 for a thermal energy supply of 50 W~200 W. In FIG. 5, the numeral TS indicates thermostat to set up a proper heating temperature (e.g. 80° C. ) for the heating element; SW indicating the switch; F being fuse; P.S. indicating power source supply; and P.L. being power lamp. The numeral C (FIG. 1) indicates a knob for adjusting the power supplied to the heating elements and for switching on (or off) the power supply.

Figure 6:
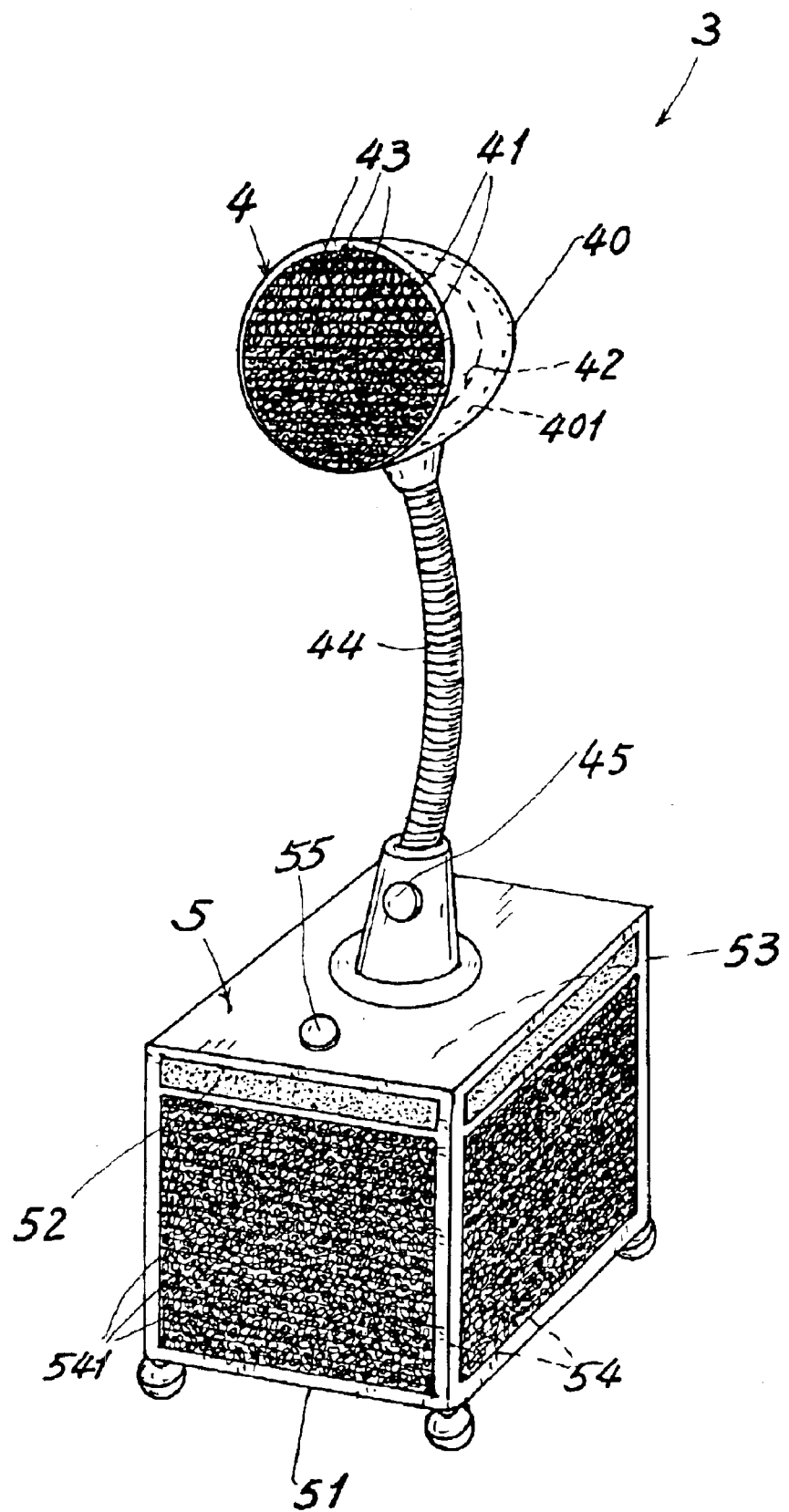
FIG. 6 is a perspective view of the juxtapositional far-infrared and anion generator of the present invention.
Figure 7:
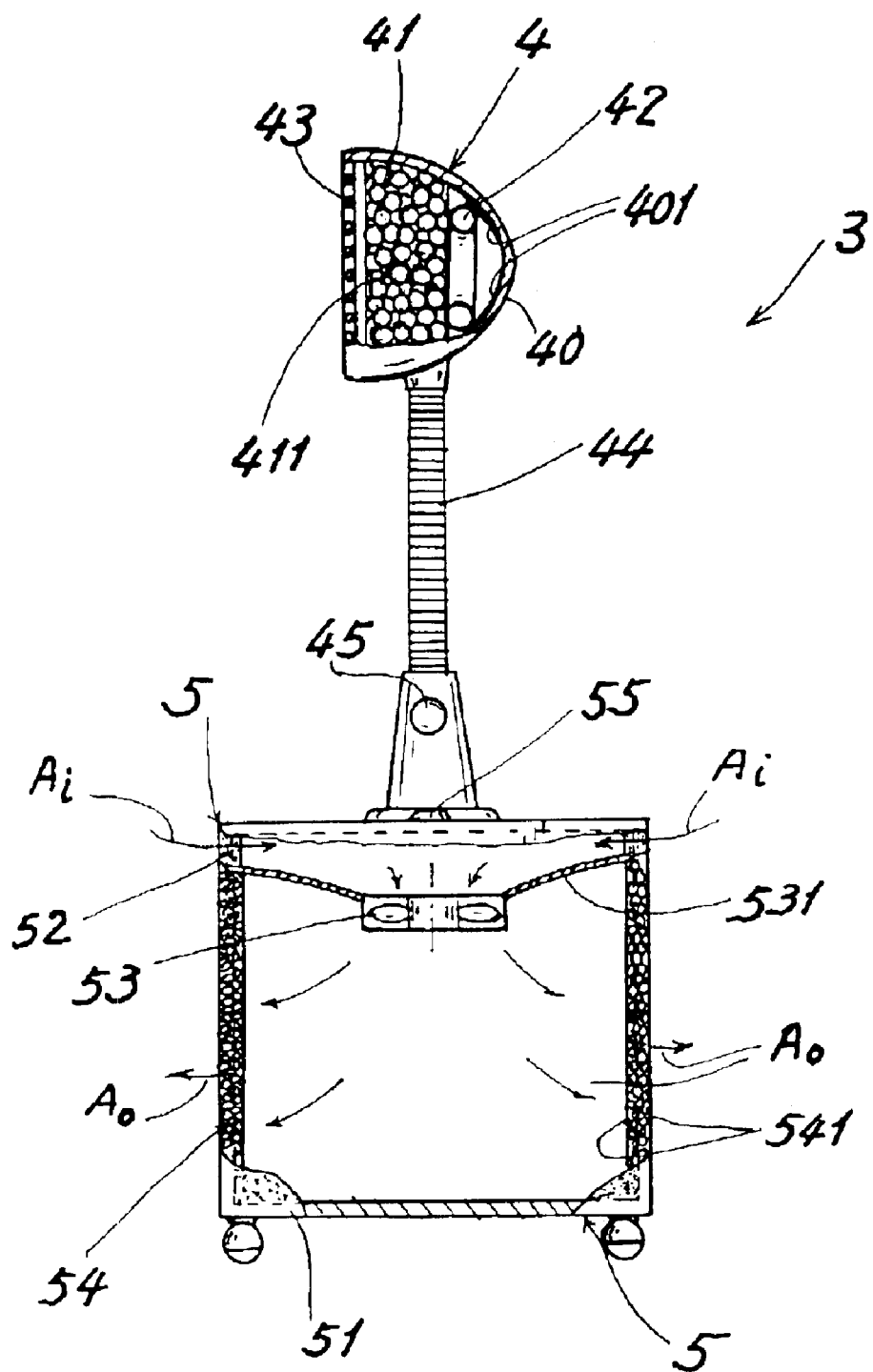
FIG. 7 is a sectional drawing of the generator as shown in FIG. 6.

The juxtapositional far-infrared and anion generator 3 as shown in FIGS. 6, 7 includes: a far-infrared lamp 4 and an anion-releasing air cleaner 5 integrally formed with the far-infrared lamp 4 for emitting far-infrared rays and releasing anions into air.

The far-infrared lamp 4 includes: a shade 40 having far-infrared radiation material including Tourmaline 41 filled in the shade 40, a heating device 42 (or a heating bulb) formed in the shade for electrically heating the far-infrared radiation material 41 for emitting far-infrared rays outwardly towards the user's body seating, leaning or lying on the massaging means 1 as shown in FIG. 1 for helpfully improving the blood circulation and metabolism of the user.

The shade 40 may further include a reflector 401 positioned behind the heating device or heating bulb 42 for reflecting the far-infrared rays outwardly towards the user's body.

The radiation material (Tourmaline) 41 may be pre-filled in a porous bag or net-like bag, which is then filled into the shade 40 of the lamp 4, having a grating front cover 43 formed on a front portion of the lamp 4. The grating of the front cover 43 may be coated or electrostatically plated with thermally insulative material to prevent from any burning injury when contacting thereto.

The lamp 4 further includes a flexible stand 44 for angularly supporting the lamp having a button or switch 45 for turning on (or off) the lamp and for controlling the temperature of the lamp.

The lamp 4 may be telescopically or foldably mounted on the anion-releasing air cleaner 5. The housing of the air cleaner 5 will serve as a "supporting base" for supporting the lamp 4.

The anion-releasing air cleaner 5 includes: a casing 51, an air fan 53 secured in a suction hood 531 formed in the casing 51 having a suction port of the fan 53 fluidically communicated with a suction filter 52 formed in the casing 51 for primarily filtering the inlet air (Ai), an outlet filter 54 secured in the casing 51 opposite to the suction filter 52 and fluidically communicated with an outlet port of the fan 53 having an anion-releasing material including Tourmaline filled in the outlet filter 54 for releasing anions into the air as outwardly discharging through the outlet filter 54 for deodorizing the outlet air (Ao) blown by the fan 53.

The Tourmaline may be filled in a porous bag or net 541 formed in the outlet filter 54. A switch or control knob 55 is formed on the casing 51 for switching on (or off) the power or for adjusting the volumetric rate of the air streamflow blown from the fan 53.

The anions as released from Tourmaline will deodorize the outlet air (Ao) as discharged from the fan 53. Also. The anions may help inhibit the bacteria growth and may activate the blood and cells in the user's body for enhancing his or her health. The suction filter 52 may be modified to further incorporate activated carbon as deodorant, fibrous cloth for filtering bacteria as laden in the inlet air, and electrostatic dust collector for removing dust, thereby preliminarily cleaning the inlet air (Ai) as sucked by the fan 53 of the air cleaner 5.

The present invention provides a health device to allow the user to be directly contacted with the massaging means 1 to be intimately radiated with far-infrared as radiated from the chair-like or bed-like massaging means 1; and to be simultaneously "treated" by the juxtapositional far-infrared and anion generator 3 for receiving the far-infrared radiation and anion-rich air supply in a "remote" way for synergetically enhancing his or her health.

The present invention may be modified without departing from the spirit and scope of the present invention.

We claim:

1. A health device comprising:
   a far-infrared massaging means formed as a seating and leaning device adapted for a user's seating and leaning thereon, and having at least a far-infrared actuation unit formed in said massaging means, having a far-infrared radiation material including Tourmaline filled in the actuation unit adapted to be contacted with the user's body for radiating far-infrared rays into the user's body as emitted from said far-infrared radiation material, and having a warming box which is formed therein with said far-infrared actuation unit filled with said far-infrared radiation material including Tourmaline in said actuation unit;

said warming box operatively radiating far-infrared from said far-infrared radiation material in said actuation unit to the user's feet and legs when inserted into said warming box; and a juxtapositional far-infrared and anion generator movably juxtapositioned to said massaging means having a far-infrared radiation and anion releasing material including Tourmaline filled in said generator for radiating far-infrared rays towards the user and for releasing anions into air to be inhaled by the user for helpfully improving the user's health, and having a far-infrared lamp and an anion-releasing air cleaner integrally formed with the far-infrared lamp for emitting far-infrared rays and releasing anions into air.

2. A health device according to claim 1, wherein said far-infrared lamp includes: a shade having far-infrared radiation material including Tourmaline filled in the shade, a heating device formed in the shade for electrically heating the far-infrared radiation material for emitting far-infrared rays outwardly towards the user's body seating, leaning or lying on the massaging means.

3. A health device according to claim 1, wherein said anion-releasing air cleaner includes: a casing, an air fan secured in a suction hood formed in the casing having a suction port of the fan fluidically communicated with a suction filter formed in the casing for primarily filtering the inlet air, an outlet filter secured in the casing opposite to the suction filter and fluidically communicated with an outlet port of the fan having an anion-releasing material including Tourmaline filled in the outlet filter for releasing anions into the air as outwardly discharging through the outlet filter for deodorizing the outlet air blown by the fan.

* * * * *